United States Patent
Hamed et al.

(10) Patent No.: US 10,978,178 B2
(45) Date of Patent: Apr. 13, 2021

(54) SYSTEMS AND METHODS FOR PROVIDING A SPECIFICITY-BASED NETWORK ANALYSIS ALGORITHM FOR SEARCHING AND RANKING THERAPEUTIC MOLECULES

(71) Applicants: Merck Sharp & Dohme Corp., Rahway, NJ (US); Merck Sharp & Dohme s.r.o., Prague (CZ)

(72) Inventors: Ahmed Abdeen Hamed, Boston, MA (US); Agata Leszczynska, Prague (CZ)

(73) Assignee: MERCK SHARP & DOHME CORP., Rahway, NJ (US)

( * ) Notice: Subject to any disclaimer, the term of this patent is extended or adjusted under 35 U.S.C. 154(b) by 289 days.

(21) Appl. No.: 16/249,753

(22) Filed: Jan. 16, 2019

(65) Prior Publication Data

US 2020/0118651 A1     Apr. 16, 2020

Related U.S. Application Data

(60) Provisional application No. 62/744,587, filed on Oct. 11, 2018.

(51) Int. Cl.
*G06F 16/2458*     (2019.01)
*G16C 20/40*     (2019.01)
(Continued)

(52) U.S. Cl.
CPC ....... *G16C 20/40* (2019.02); *G06F 16/24578* (2019.01); *G06N 20/00* (2019.01); *G16C 20/70* (2019.02)

(58) Field of Classification Search
CPC ... G16C 20/70; G16C 20/40; G06F 16/24578; G06N 20/00
(Continued)

(56) References Cited

U.S. PATENT DOCUMENTS

| | | | | |
|---|---|---|---|---|
| 6,332,138 B1* | 12/2001 | Hull | ....... | G16C 20/70 |
| | | | | 707/741 |
| 2002/0004792 A1* | 1/2002 | Busa | ....... | G16B 40/00 |
| | | | | 706/50 |

(Continued)

OTHER PUBLICATIONS

Wren et al., "Shared relationship analysis: ranking set cohesion and commonalities within a literature derived relationship network", Jan. 22, 2004, Bioinformatics, vol. 20, Issue 2, pp. 191-198. (Year: 2004).*

(Continued)

*Primary Examiner* — Mohammad S Rostami
*Assistant Examiner* — Robert F May
(74) *Attorney, Agent, or Firm* — Fenwick & West LLP

(57) ABSTRACT

A system and a method are disclosed for searching and ranking molecules based on specificity. To this end, a processor receives a request to search for molecules that correspond to biological features, and generates a mapping of molecules to the biological features by searching publications for a reference to a biological feature in connection with a molecule, and responsively adding to the mapping any found references. The processor determines a respective specificity score for each respective molecule of the plurality of molecules by determining which of the plurality of biological features are mapped to each respective molecule, and for each such respective biological feature, in response to determining that there is not more than one concrete instance that is mapped to the respective molecule, incrementing the respective specificity score by a unit. The processor generates a ranking based on the respective specificity scores and outputs the ranking.

20 Claims, 5 Drawing Sheets

(51) Int. Cl.
G06F 16/2457 (2019.01)
G06N 20/00 (2019.01)
G16C 20/70 (2019.01)

(58) Field of Classification Search
USPC .......................................................... 707/723
See application file for complete search history.

(56) References Cited

U.S. PATENT DOCUMENTS

| | | | | |
|---|---|---|---|---|
| 2004/0078211 | A1* | 4/2004 | Schramm-Apple | G09B 5/00 705/2 |
| 2005/0004785 | A1* | 1/2005 | Temkin | G16B 50/00 703/11 |
| 2010/0010747 | A1* | 1/2010 | Kinoshita | G16B 5/00 702/19 |
| 2012/0109966 | A1* | 5/2012 | Liang | G06F 16/338 707/740 |
| 2012/0296880 | A1* | 11/2012 | Chen | G16B 50/00 707/692 |
| 2015/0332158 | A1* | 11/2015 | He | G16H 70/40 706/52 |

OTHER PUBLICATIONS

Burr Settles, "ABNER: an open source tool for automatically tagging genes, proteins and other entity names in text", Apr. 28, 2005, Bioinformatics, vol. 21, Issue 14, pp. 3191-3192. (Year: 2005).*
Junker et al., "Exploration of biological network centralities with CentiBiN", Mar. 5, 2012, Bioinformatics, vol. 28, Issue 8, pp. 1178-1179. (Year: 2012).*
Degtyarenko et al. "ChEBI: An Open Bioinformatics and Cheminformatics Resource", Jun. 2009, Current Protocols in Bioinformatics, Chapter 14 (Year: 2009).*
Bragazzi et al., "A Leader Genes Approach-based Tool for Molecular Genomics: From Gene-ranking to Gene-network Systems Biology and Biotargets Predictions", Jul. 2013 Journal of Computer Science & Systems Biology (Year: 2013).*
Ahmed Abdeen Hamed, "MolecRank: A Molecule Ranking Algorithm for Mining Biological Semantic Networks", Feb. 15, 2018, University of Economics and Business Prague Department of Information and Knowledge Engineering Seminars (Year: 2018).*
Ashburner, M. et al., "Gene Ontology: tool for the unification of biology," Nature Genetics, May 2000,pp. 25-29, vol. 25, No. 1.
Bajusz, D. et al., Why is Tanimoto index an appropriate choice for fingerprint-based similarity calculations? Journal of Cheminformatics, Dec. 2015,13pages, vol. 7, No. 1.
Bodnarchuk, M.S. et al., "Role of Deprotonation Free Energies in $pK_a$ Prediction and Molecule Ranking," Journal of Chemical Theory and Computation, Jun. 2014, pp. 2537-2545, vol. 10, No. 6.
Bragazzi, N.L. et al., "A Leader Genes Approach-based Tool for Molecular Genomics: From Gene-ranking to Gene-network Systems Biology and Biotargets Predictions," J Comput Sci Syst Biol, 2013, pp. 165-176, vol. 6.
Candan, K. S. et al. "Resource Description Framework: Metadata and Its Applications," ACM SIGKDD Explorations Newsletter, Jul. 2001, pp. 6-19, vol. 3, No. 1.
Caro, L. et al. "Effect of Hepatic Impairment on the Pharmacokinetics of Grazoprevir, a Hepatitis C Virus Protease Inhibitor," Antimicrobial Agents and Chemotherapy, Dec. 2017,nine pages, vol. 61, No. 12.
Chen, J. et al., "Ranking Medical Terms to Support Expansion of Lay Language Resources for Patient Comprehension of Electronic Health Record Notes: Adapted Distant Supervision Approach," JMIR Medical Informatics, Oct. 2017, 14 pages, vol. 5, No. 4.
De Matos, P. et al., "ChEBI: a chemistry ontology and database," Journal of Cheminformatics, May 4, 2010, one page, vol. 2, No. 1.
Degtyarenko, K. et al., "ChEBI: An Open Bioinformatics and Cheminformatics Resource," Current Protocols in Bioinformatics, Jun. 2009, pp. 14.9.1-14.9.20, vol. 26, No. 1.
Degtyarenko, K. et al., "ChEBI: a database and ontology for chemical entities of biological interest," Nucleic Acids Research, Oct. 11, 2007, pp. D344-D350, vol. 36.
Gene Ontology Consortium, "The Gene Ontology (GO) database and informatics resource," Nucleic Acids Research, Jan. 2004, pp. D258-D261, vol. 32, No. 1.
Gervais, F. G. et al., "Pharmacological Characterization of MK-7246, a Potent and Selective CRTH2 (Chemoattractant Receptor-Homologous Molecule Expressed on T-Helper Type 2 Cells) Antagonist," Molecular Pharmacology, Jan. 2011, pp. 69-76, vol. 79, No. 1.
Hastings, J. et al., "The ChEBI reference database and ontology for biologically relevant chemistry: enhancements for 2013," Nucleic Acids Research, Jan. 2013, pp. D456-D463, vol. 41, No. D1.
Hastrup, N. et al., "The effects of the CXCR2 antagonist, MK-7123, on bone marrow functions in healthy subjects," Cytokine, Apr. 2015, pp. 197-203, vol. 72, No. 2.
Hiett, J. A. et al., "Topical Carbonic Anhydrase Inhibitors: A New Perspective in Glaucoma Therapy," Optometry clinics: the official publication ofthe Prentice Society, 1992, pp. 97-112, vol. 2, No. 4.
Hopkins, A., "Network pharmacology: the next paradigm in drug discovery," Nature Chemical Biology, Nov. 2008, pp. 682-690, vol. 4, No. 11.
Hostetler, E. D. et al., "Evaluation of [$^{18}$F]MK-0911, a positron emission tomography (PET) tracer for opioid receptor-like 1 (ORL1), in rhesus monkey and human," NeuroImage, Mar. 2013, 10 pages, vol. 68.
Junker, B. H. et al., "Exploration of biological network centralities with CentiBiN," BMC Bioinformatics, Apr. 21, 2006, seven pages, vol. 7, No. 219.
Kibbe, W. A. et al., "Disease Ontology 2015 Update: an expanded and updated database of human diseases for linking biomedical knowledge through disease data," Nucleic Acids Research, Jan. 2015, pp. D1071-D1078, vol. 43, No. D1.
Koschutzki, D. et al., "Ranking of network elements based on functional substructures," Journal of Theoretical Biology, Oct. 2007, pp. 471-479, vol. 248, No. 3.
Lynch, J. J. et al., "Nonpeptide Glycoprotein IIb/IIIa Inhibitors. 5. Antithrombotic Effects of MK-0383," Journal of Pharmacology and Experimental Therapeutics, Jan. 1995,pp. 20-32,vol. 272, No. 1.
Meininger, G. E. et al., "Effects of MK-0941, a Novel Glucokinase Activator, on Glycemic Control in Insulin-Treated Patients with Type 2 Diabetes," Diabetes Care, Dec. 2011, pp. 2560-2566, vol. 34, No. 12.
NIH U.S. National Library of Medicine, "An Efficacy and Safety Trial of Verubecestat (MK-8931) in Mild to Moderate Alzheimer's Disease (P07738) (EPOCH)," Dec. 2012, 68 pages, [Online] [Retrieved on Apr. 30, 2019], Retrieved from the Internet <URL: https://clinicaltrials.gov/ct2/show/NCT01739348#wrapper>.
Osborne, J.D. et al., "Annotating the human genome with Disease Ontology," BMC Genomics, Jul. 2009, eight pages, vol. 10, No. 1.
Ramjit, D. R. et al. "Antithrombotic Effects of MK-0852, a Platelet Fibrinogen Receptor Antagonist, in Canine Models of Thrombosis," Journal of Pharmacology andExperimental Therapeutics, Sep. 1993,pp. 1501-1511, vol. 266, No. 3.
Schriml, L.M. et al., "Disease Ontology: a back-bone for disease semantic integration," Nucleic Acids Research, Jan. 2012, pp. D940-D946, vol. 40, No. D1.
Settles, B., "ABNER: an open source tool for automatically tagging genes, proteins, and other entity names in text," Bioinformatics, Apr. 28, 2005, pp. 3191-3192, vol. 21, No. 14.
Shannon, C.E., "Prediction and Entropy of Printed English," Bell Labs Technical Journal, Jan. 1951, pp. 50-64, vol. 30, No. 1.
Weston, J. et al., "Protein ranking: From local to global structure in the protein similarity network," Proceedings of the National Academy of Sciences, Apr. 27, 2004, pp. 6559-6563, vol. 101, No. 17.
Winter, C. et al., "Google Goes Cancer: Improving Outcome Prediction for Cancer Patients by Network-Based Ranking of Marker Genes," PLoS Computational Biology, May 2012, 16 pages, vol. 8, No. 5.

(56) References Cited

OTHER PUBLICATIONS

Wolkenberg, S. E. et al., "Discovery of MK-1832, a Kv1.5 inhibitor with improved selectivity and pharmacokinetics," Bioorganic & Medicinal Chemistry Letters, Feb. 15, 2017, pp. 1062-1069, vol. 27, No. 4.

Wren, J.D. et al., "Shared relationship analysis: ranking set cohesion and commonalities within a literature-derived relationship network," Bioinformatics, Jan. 2004, pp. 191-198, vol. 20, No. 2.

Zahoránszky-Kőhalmi, G. et al., "Impact of similarity threshold on the topology of molecular similarity networks and clustering outcomes," Journal of Cheminformatics, Dec. 2016, 17 pages, vol. 8, No. 1.

Zhang, B. et al., "Erratum to: Design of chemical space networks using a Tanimoto similarity variant based upon maximum common substructures," Journal of Computer-Aided Molecular Design, Nov. 2015, pp. 1071-1072, vol. 29, No. 11.

\* cited by examiner

| Ranking | MK-Number | Disease | Cell Type | Gene | Protein |
|---|---|---|---|---|---|
| 2 | MK1 | alzheimer's | brain | ---- | p53 |
| 4 | MK2 | disease | ---- | ---- | [p53, leptin] |
| 1 | MK3 | breast cancer | breast | BRCA1 | EML4 |
| 3 | MK4 | lung cancer | ---- | ---- | p53 |
| 5 | MK5 | diabetes | ---- | ---- | {P110α, Leptin, EML4} |

FIG. 2

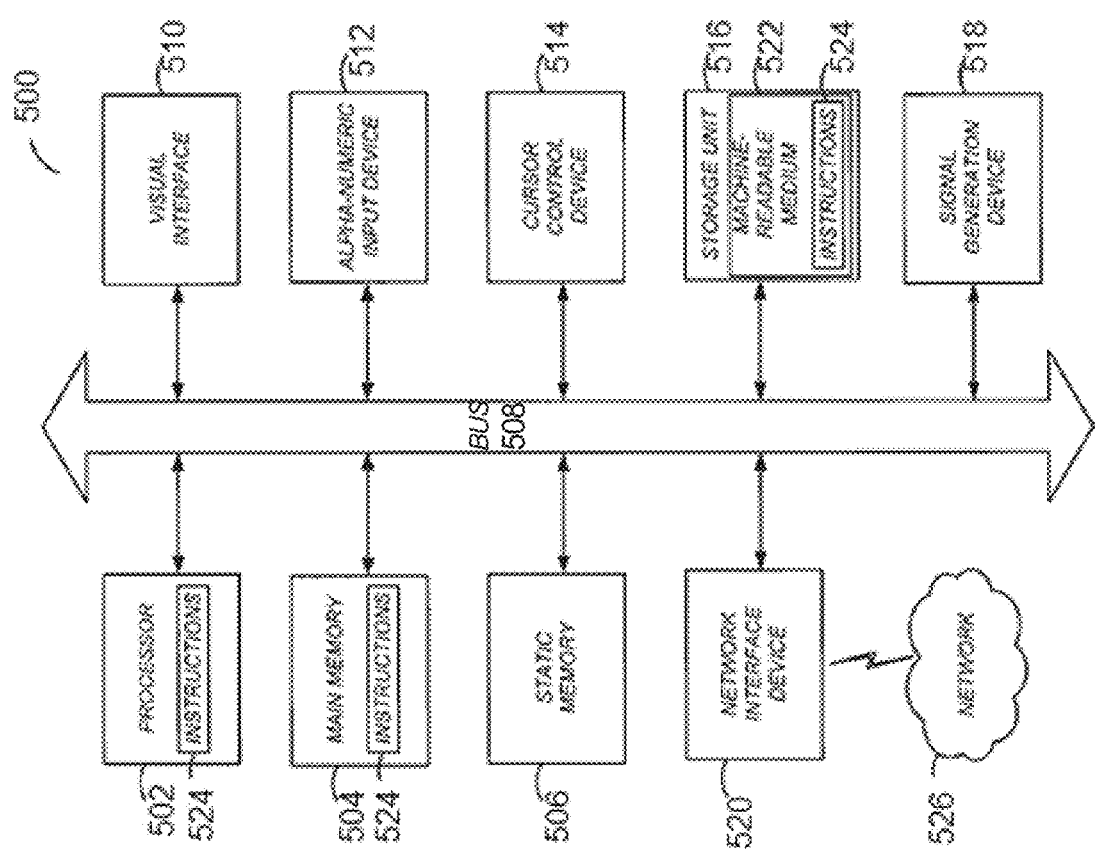

SYSTEMS AND METHODS FOR PROVIDING A SPECIFICITY-BASED NETWORK ANALYSIS ALGORITHM FOR SEARCHING AND RANKING THERAPEUTIC MOLECULES

CROSS REFERENCE TO RELATED APPLICATIONS

This application claims the benefit of U.S. Provisional Application No. 62/744,587 filed Oct. 11, 2018, the disclosure of which is hereby incorporated by reference herein in its entirety.

TECHNICAL FIELD

The disclosure generally relates to the field of ranking chemistry molecules, such as therapeutic molecules, based on data scraped and analyzed from medical literature. More particularly, the disclosure describes systems and methods for providing a specificity-based network analysis algorithm for searching and ranking molecules.

BACKGROUND

In some embodiments, the systems and methods disclosed herein seek to aid scientists in a search for therapeutic molecules that are most likely to be applicable for treating issues that exhibit specific biological features. Related art systems that rank biological terms do not allow for a search targeted based on specificity. Rather, related art systems that rank genes will lift genes higher in a ranking if many sources point to that gene as relevant, without reference to whether that gene specifically applies to the scientist's issue. Other related art systems rely on centrality measures to identify the most influential elements in a network, again without regard to aiding a scientist to find a most specific molecule to the scientist's needs.

BRIEF DESCRIPTION OF DRAWINGS

The disclosed embodiments have other advantages and features which will be more readily apparent from the detailed description, the appended claims, and the accompanying figures (or drawings). A brief introduction of the figures is below.

FIG. 2 illustrates one embodiment of a table of mappings between molecules and concrete instances of various biological features, as well as a specificity-based ranking of those molecules, in accordance with some embodiments of the disclosure.

FIG. 5 illustrates one embodiment of a block diagram illustrating components of an example machine able to read instructions from a machine-readable medium and execute them in a processor (or controller).

DETAILED DESCRIPTION

Figure 1:
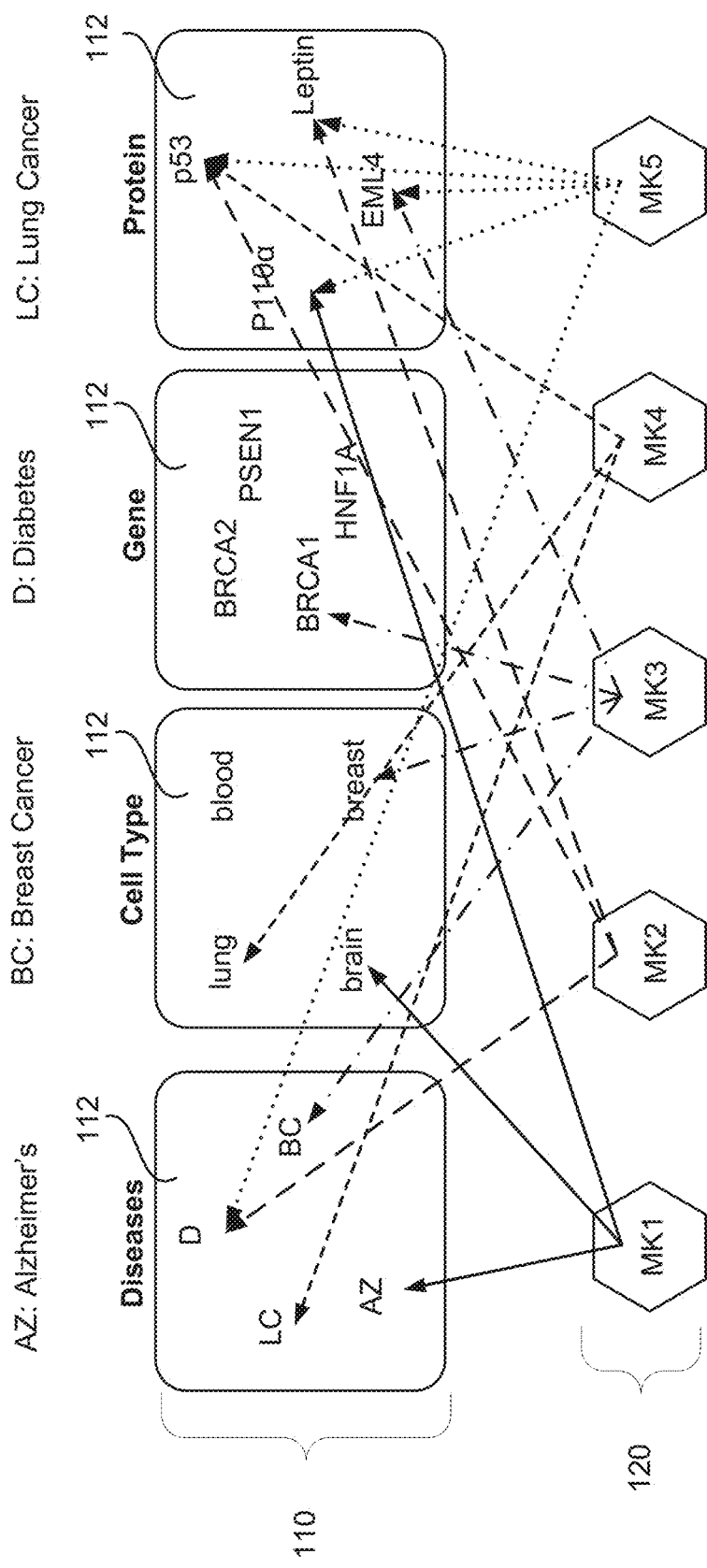
FIG. 1 illustrates one embodiment of a network of mappings between molecules and concrete instances of various biological features, in accordance with some embodiments of the disclosure.

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

One embodiment of a disclosed system, method and computer readable storage medium includes a mechanism that enables an entity to procure a ranked list of drugs that binds (and in some cases, only binds) to very particular cells. Such a specificity-based mechanism enables the entity to view drugs that would be suited to solve a physiological problem, while minimizing side effects. By way of example, the mechanism may search medical literature for mentions of, or references to, biological features that were input by the entity. The mentions (or references—the terms "mention" and "reference" are used interchangeably herein) may include a reference to a molecule, and a particular concrete instance of the biological feature. These mentions may be analyzed for specificity of the molecule (e.g., based inversely on the number of concrete instances mentioned in association with the molecule). A ranked list of molecules is then presented to the entity in order of specificity.

More particularly, systems, methods, and a computer readable storage medium with instructions (or program code or software) encoded thereon are disclosed herein. The systems and methods further may be carried out through a processor (one or more) that executes the instructions. Description to processor configurations herein would be in the context of the processor executing instructions to undertake the particular configuration described.

The instructions, when executed, causes the processor to receive a request to search for molecules that correspond to a pre-specified plurality of biological features. The processor generates a data structure that maps a plurality of molecules to the plurality of pre-specified biological features. The processor may perform this generation by searching publications for a mention of a concrete instance corresponding to a biological feature of the pre-specified plurality of biological features in connection with a molecule, and adding a mapping between a given molecule, a given biological feature, and a given concrete instance to the data structure when such a mention is found.

The processor goes on to determine a respective specificity score for each respective molecule of the plurality of molecules. This determination is performed by, for each respective molecule of the plurality of molecules, determining which of the plurality of biological features are mapped to the respective molecule, and, for each such respective biological feature, determining whether more than one concrete instance corresponding to the respective specified biological feature is mapped to the respective molecule. The processor, in response to determining that there is not more than one concrete instance corresponding to the respective biological feature that is mapped to the respective molecule, increments the respective specificity score by a unit.

The processor thereafter may generate a ranking of the plurality of molecules based on each respective specificity score for each respective molecule of the plurality of molecules. For example, a molecule with a highest specificity score will be ranked highest, followed by a next highest specificity score, and so on. The processor ultimately outputs the ranking (e.g., by generating the ranking in displayable format and transmitting the ranking to a display apparatus).

Computer-implemented methods, systems, and computer-readable instructions are disclosed herein for searching and ranking molecules based on specificity. A processor receives a request to search for molecules that correspond to a pre-specified plurality of biological features, and generates a data structure that maps a plurality of molecules to the plurality of pre-specified biological features by searching publications for a reference to a concrete instance corresponding to a biological feature of the pre-specified plurality of biological features in connection with a molecule, and in response to detecting, during the searching, a given reference to a given concrete instance corresponding to a given biological feature in connection with a given molecule, adding a mapping between the given molecule, the given biological feature, and the given concrete instance to the data structure.

The processor determines a respective specificity score for each respective molecule of the plurality of molecules by determining which of the plurality of biological features are mapped to the respective molecule, and, for each respective biological feature of the plurality of biological features that are mapped to the respective molecule, determining whether more than one concrete instance corresponding to the respective specified biological feature is mapped to the respective molecule and in response to determining that there is not more than one concrete instance corresponding to the respective biological feature that is mapped to the respective molecule, incrementing the respective specificity score by a unit. The processor generates a ranking of the plurality of molecules based on each respective specificity score for each respective molecule of the plurality of molecules, and outputs the ranking.

In some embodiments, when searching publications for a reference to a concrete instance corresponding to a biological feature of the pre-specified plurality of biological features in connection with a molecule, the processor transmits the pre-specified plurality of biological features into an ontology, receives an output of additional biological features from the ontology, and searches publications for a reference to either a concrete instance corresponding to a biological feature of the pre-specified plurality of biological features in connection with a molecule, or a reference to a concrete instance corresponding to an additional biological feature of the additional biological features in connection with a molecule.

In some embodiments, the processor, when searching publications for a reference to a concrete instance corresponding to a biological feature of the pre-specified plurality of biological features in connection with a molecule, applies a machine learning algorithm to detect an obscured reference to a concrete instance corresponding to a biological feature of the pre-specified plurality of biological features in connection with a molecule, notwithstanding that the obscured reference neither matches a pre-specified biological feature of the plurality of biological features nor an additional biological feature of the additional biological features.

In some embodiments, when determining the respective specificity score for each respective molecule of the plurality of molecules further, the processor, in response to determining that there is more than one concrete instance corresponding to the respective biological feature that is mapped to the respective molecule, determines a number of concrete instances corresponding to the respective biological feature that is mapped to the respective molecule, and increments the respective specificity score by an amount smaller than the unit, wherein the amount is inversely proportional to the number.

In some embodiments, when generating the ranking of the plurality of molecules, the processor determines a reputation score for each publication in which each respective molecule of the plurality of molecules was referenced, generates weighted specificity scores by applying a weight to each respective specificity score of each respective molecule based on an aggregation of each reputation score corresponding to a publication in which the respective molecule was referenced, and generates the ranking based on the weighted specificity scores.

In some embodiments, further in response to detecting, during the searching, a reference to a given concrete instance corresponding to a given biological feature in connection with a given molecule, the processor determines whether a respective reputation score from a publication comprising the reference exceeds a threshold, where adding the mapping between the given molecule, the given biological feature, and the given concrete instance to the data structure is performed in response to determining that the respective reputation score exceeds the threshold. In response to determining that the respective reputation score does not exceed the threshold, the processor refrains from adding the mapping between the given molecule, the given biological feature, and the given concrete instance to the data structure.

In some embodiments, further in response to detecting, during the searching, a given reference to a given concrete instance corresponding to a given biological feature in connection with a given molecule, the processor determines whether the given reference indicates an adverse drug reaction in connection with the given molecule. In response to determining that the given reference indicates an adverse drug reaction in connection with the given molecule, the processor includes a flag in the mapping corresponding to the given molecule. Outputting the ranking to the user may comprise adjusting the ranking to reduce the rank of the given molecule based on the flag, and outputting the adjusted ranking.

In some embodiments, when generating the ranking, the processor determines a number of publications in which a molecule of the plurality of molecules, a biological feature, and a concrete instance are referenced in connection with one another, and increases the ranking of the molecule relative to other molecules of the plurality of molecules based on the number of publications.

In some embodiments, the publications were pre-searched based on common biological features, and wherein a graph was created that maps pre-searched biological features to molecules and concrete instances. When searching the publications for the reference to a concrete instance corresponding to a biological feature of the pre-specified plurality of biological features in connection with a molecule comprises, the processor may determine whether the pre-specified plurality of biological features comprise a common biological feature, and, in response to determining that the pre-specified plurality of biological features comprise the common biological feature, the processor searches the graph instead of the publications themselves.

In some embodiments, in response to determining that the pre-specified plurality of biological features does not comprise the common biological feature, the processor searches the publications themselves, and, in response to detecting, during the searching, a given reference to a given concrete instance corresponding to a given biological feature in connection with a given molecule, the processor adds the mapping to the graph.

Determining Specificity

Referring now to FIG. 1, it illustrates one embodiment of a network of mappings between molecules and concrete instances of various biological features, in accordance with some embodiments of the disclosure. FIG. 1 depicts biological features 110, each of which include concrete instances 112. FIG. 1 also includes molecules 120, as well as mappings between the molecules 120 and various concrete instances 112. As used herein, a biological feature, such as those included in biological features 110, is a type of biological component, such as a disease, a cell type, a gene, a protein, and the like. Another way of stating the manner in which the term biological feature is used is as a macro category. For example, a disease is a biological feature, and is a macro category of concrete instances 110, such as lung cancer (depicted as "LC" in FIG. 1), breast cancer (depicted as "BC" in FIG. 1), and other diseases.

The term concrete instance, as used herein, is a specific instance of a biological feature, or, in other words, an occurrence that can be classified within the category that the biological feature covers. The term molecule, as used herein, is a molecular structure that, when applied to a concrete instance, results in a change in the concrete instance. For example, if molecule MK1 of molecules 120 is applied to Alzheimer's disease, then the effects of Alzheimer's disease are reduced—and thus, there has been a change in the concrete instance. The term "molecule" herein may be used interchangeably with the term "drug" herein in the context of addressing physiological (or biological) treatments.

In connection with searching and ranking molecules based on specificity, a processor (as described in further detail below with respect to FIG. 5) receives a request to search for molecules that correspond to a pre-specified plurality of biological features. In some embodiments, the processor receives the request from a client device, where the user indicates the pre-specified plurality of biological features by specifying biological features 110, such as diseases, cell type, gene, and protein, into a form displayed at the client device. As either a supplement to the user-indicated biological features, or as a separate embodiment, a computer or application generates the request, where the computer or application determines the biological features (e.g., based on user-input parameters, or based on machine-input parameters, such as parameters iteratively generated based on machine learning).

The processor, having received the request, generates a data structure that maps a plurality of molecules to the plurality of pre-specified biological features based on mentions in publications. The mapping is a logical link, such as a pointer, hierarchical structure, link, or set of fields, that connects each molecule to associated ones of pre-specified biological features. For example, the data structure may be a graph, such as that illustrated in FIG. 1, a table, such as that illustrated in FIG. 2 (to be described in further detail below), or any other type of data structure. As depicted in FIG. 1, various molecules 120 are mapped to various ones of the pre-specified biological features 110. For example, MK1 is mapped to the following biological features: Diseases, Cell Type, and Protein. This mapping can be seen based on the arrows connecting MK1 with each of these biological instances.

In connection with generating the data structure, the processor may search publications for a mention of a concrete instance corresponding to a biological feature of the pre-specified plurality of biological features in connection with a molecule. As used herein, the term publications refers to any writing relating to molecules, such as medical, scientific, and academic literature, that is captured on an electronic storage medium. The publication may be stored on a database on the electronic storage medium and may be searchable. Publications need not be formal writings; any writing may qualify, such as a social media publication (e.g., by a social media platform such as FACEBOOK, LINKEDIN, and the like), a publication through a blog or other Internet publication service, and the like.

The processor may determine that a request restricts what types of publications may be searched. For example, a user may indicate in a form displayed at a client device that only academic literature is to be searched, in which case other forms of publications may be ignored. The processor may cause the form to indicate myriad selectable restrictions, such as based on author, platform, university or hospital name, publications that have been rated or viewed at a threshold level, and the like. The processor also may restrict what publications are searched automatically based on default or user-set parameters, or based on past interactions by a user. The processor may search a central database of publications, or may search myriad publication databases (e.g., databases distributed across university and hospital networks; databases of social media networks, etc.).

To generate the data structure, when a given mention is detected of a given concrete instance corresponding to a given biological feature in connection with a given molecule, the processor adds a mapping between the given molecule, the given biological feature, and the given concrete instance to the data structure. For example, as seen in FIG. 1, MK2 includes a mapping to the concrete instance diabetes. That mapping doubles as a mapping to the biological feature of diseases, as the arrow from MK2 to Diabetes also points to the Diseases biological feature. This mapping may have been added because of a sentence in a medical publication that states that "MK2 is known to treat diabetes," where the processor determines that diabetes corresponds to disease, and is mentioned in connection with MK2. The determination that diabetes is mentioned in connection with MK2 may be made by the processor based on use of a model that maps sentence structure into connectivity between terms.

The term "mention," as used herein, refers to text where a processor detects a molecule and concrete instance in near proximity to one another. In an embodiment, the processor detects such a mention by running candidate text through a Resource Descriptor Framework (RDF), which maps text to template mentions to determine whether the text qualifies as a mention as meant herein. For example, a template may be that a mention is found if "Breast cancer" co-occurs (e.g., in a same sentence or paragraph) with "BT-549."

In some embodiments, when searching publications for a mention of a concrete instance corresponding to a biological feature of the pre-specified plurality of biological features in connection with a molecule, the processor may feed the pre-specified plurality of biological features into an ontology. The term ontology, as used herein, refers to a thesaurus-like tool that maps biological features to alternate ways of stating the biological feature (e.g., "disease" may be mapped to "illness"), or to highly related biological features. An ontology may thus be used to supplement the terms input by way of the request (e.g., from the user, or from an application). The processor may feed the pre-specified plurality of biological features by default, or based on input by a user or application that requests that input biological features be supplemented based on the ontology.

When an ontology is used, the processor receives an output of additional biological features from the ontology, and searches publications for a mention of either a concrete instance corresponding to a biological feature of the pre-specified plurality of biological features in connection with a molecule, or a mention of a concrete instance corresponding to an additional biological feature of the additional biological features in connection with a molecule, thus supplementing the pre-specified biological features with additional, related biological features to form a more robust search.

In some embodiments, the processor may go beyond using the ontology to supplement the pre-specified biological features, and may additionally apply a machine learning algorithm to detect an obscured mention of a concrete instance corresponding to a biological feature of the pre-specified plurality of biological features in connection with a molecule, notwithstanding that the obscured mention neither matches a pre-specified biological feature of the plurality of biological features nor an additional biological feature of the additional biological features. For example, a machine learning algorithm may learn that when a set of words are placed between a molecule and a noun, that set of words indicates that the noun is a concrete instance that corresponds to a pre-specified biological feature. Thus, the processor may use the machine learning algorithm to detect a biological feature that is to be mapped even if a concrete instance is encountered that is neither known to correspond to a pre-specified biological feature nor to one identified by an ontology.

Following the generation of the mapping, the processor determines a specificity score for each respective molecule of the plurality of molecules. The manner in which the processor determines the specificity score will be explained with reference to FIG. 2. FIG. 2 illustrates one embodiment of a table of mappings between molecules and concrete instances of various biological features, as well as a specificity-based ranking of those molecules, in accordance with some embodiments of the disclosure. As described above, table 200 is an alternate form of data structure from that depicted in FIG. 1. Table 200 includes molecules 220, which correspond to molecules 120 of FIG. 1. Table 2 also includes diseases 230, cell types 240, genes 250, and proteins 260, each of which correspond to their counterparts within biological features 110. Each row of table 200 represents a mapping of each of biological features 110 (that is, disease 230, cell type 240, gene 250, and protein 260), the mapping being indicated by concrete instances named on each row.

The processor may determine the specificity score for a given molecule of molecules 120 by determining which of the plurality of biological features are mapped to the respective molecule. For example, the processor may determine that MK1 is mapped to a disease, a brain, and a protein, based on concrete instances being named for each of those biological features in table 200. The processor may, as another example, determine that MK2 is mapped to a disease and to a protein, on the same basis.

Continuing with calculating the specificity score, the processor may, for each respective biological feature of the plurality of biological features that are mapped to the respective molecule, determine whether more than one concrete instance corresponding to the respective specified biological feature is mapped to the respective molecule. For example, the processor may determine that for molecule MK1, only one concrete instance is mapped to each biological feature (e.g., Disease is only mapped to Alzheimer's; Cell Type is only mapped to brain, and Protein is only mapped to p53). For molecule MK2, the processor may determine that while only one concrete instance is mapped to disease, two concrete instances are mapped to protein (e.g., Disease is only mapped to diabetes, but Protein is mapped to both p53 and leptin).

The processor, in response to determining that there is not more than one concrete instance corresponding to the respective biological feature that is mapped to the respective molecule, increments the respective specificity score by a unit. Thus, following the example above, the processor would increment the specificity score for molecule MK1 by 3 units because each of disease, cell type, and protein only have one concrete instance mapped to them. The processor would increment the specificity score for molecule MK2 by only 1 unit, despite molecule MK2 corresponding to two biological features, because the Protein biological instance corresponds to more than one concrete instance.

After performing the above specificity score calculation for each molecule found during the searching, the processor generates a ranking of the plurality of molecules based on each respective specificity score for each respective molecule of the plurality of molecules. Assuming an initialization of the specificity score to zero units, and following the example in table 200 and in the above description, the processor would calculate the specificity score for each molecule depicted in table 200 as follows:

Molecule MK1 would have a specificity score of 3 units, as described above.

Molecule MK2 would have a specificity score of 1 unit, as described above

Molecule MK3 would have a specificity score of 4 units, given that all four pre-specified biological features have exactly one concrete instance mapped to them and to molecule MK3.

Molecule MK4 would have a specificity score of 2 units, given that two pre-specified biological features—disease and protein—each have one concrete instance mapped to them and to the molecule—lung cancer and p53, respectively.

Molecule MK5 would have a specificity score of 1 unit, given that only one pre-specified biological feature—disease—has one concrete instance mapped to it—namely, diabetes. While protein is also mapped to MK5, there are three concrete instances of protein within the mapping—namely, P110a, Leptin, and EML4. Because there is more than one concrete instance of protein within the mapping, the specificity score is not incremented for a unit based on a protein being mapped to MK5.

Based on these calculated specificity scores, the processor ranks molecules 220, as is depicted in ranking 210 of table 200, from the highest specificity score to the lowest specificity score. Note that while MK2 and MK5 appear to be tied for the fourth rank as they each have a specificity score of 1 unit, in some embodiments, additional factors go into the processor's specificity calculation, which are explained below, which may act to break a tie based on the aforementioned process alone.

After calculating the specificity scores, the processor outputs the ranking. In some embodiment, the processor generates for display a list of molecules in the ranked order, enabling a user at a client device to view the ranked list. In some embodiments, the processor transmits the ranked list to an application, which may apply further processing to the ranked list for whatever purpose. The processor may additionally, or alternatively, cause the ranked list to be stored to memory for future use.

As mentioned above, the processing circuitry may factor additional parameters into calculating the specificity score for each respective molecule of the plurality of molecules. In some embodiments, the processor may increment the specificity score of a molecule based on a mapping between the molecule and a pre-specified biological feature (as potentially supplemented by an ontology or machine learning) notwithstanding that multiple concrete instances are mapped to that biological feature in connection with the molecule. To this end, the processor may determine a number of concrete instances corresponding to the respective biological feature that is mapped to the respective molecule, and may increment the respective specificity score by an amount smaller than the unit, wherein the amount is inversely proportional to the number. For example, MK2 and MK5, as described above, are each awarded an increment of one unit to their specificity scores for their having one concrete instance within the biological feature "disease."

In some embodiments, the processor may determine the ranking of the plurality of molecules based on factors additional to the specificity score alone. In some embodiments, the processor determines a reputation score for each publication in which each respective molecule of the plurality of molecules was mentioned. The term reputation score, as used herein, is a score representing how a community perceives a publication, a source of a publication, or an aggregated perception of both the publication itself and the source of the publication. The processor may determine how a publication is perceived based on any trackable statistic corresponding to the publication, such as how many times, or how frequently, the publication is accessed, a degree to which the publication is cited in other works (or in other reputable works), and the like. The processor may determine how a source of a publication is perceived based on how many other domains point to that source, a degree to which publications from the source are cited in other reputable publications, and the like. For example, a value may be derived from the perception by determining what citations were made to the publication, by whom, when, and/or frequency. Moreover, as the referring sources, e.g., another publication and/or entity (e.g., an individual), may have an associated reputational or reference score that may be factored in as, for example, a weighted value. The weighted values may provide a basis for a scoring system that corresponds to a perception ranking and/or ordering. If multiple mentions were made of the molecule in connection with a concrete instance of a biological feature, and thus caused to be added to the mapping, the processor calculates reputation scores for each publication including a mention.

The processor may factor the reputation score into the ranking by generating weighted specificity scores where a weight is applied to each respective specificity score of each respective molecule based on an aggregation of each reputation score corresponding to a publication in which the respective molecule was mentioned. The aggregation may be a statistical manipulation, such as an average, median, mean, or mode of each reputation score. In some embodiments, the processor may apply a weighting that is directly proportional to the reputation score, where a higher reputation score indicates a higher degree to which a publication is perceived. In some embodiments, the processor may limit the application of the weighting to a specificity score to scenarios where a reputation score is low (e.g., below a threshold), where, when the processor determines that a reputation score is low, a specificity score is discounted. The discount may be a constant discount whenever a reputation score is below a threshold, or may be discounted by an amount that is proportional to the reputation score. The processor thereafter generates the ranking based on the weighted specificity scores.

While the systems and methods discussed above describe the processor adding a mapping whenever a qualifying mentioned is encountered during the searching, in some embodiments, the processor may refrain from adding a mapping to the data structure solely based on this criterion. Rather, when such a mention is encountered in the search, the processor may determine whether a reputation score of the publication in which the mention is encountered exceeds a threshold. The processor may add the mapping in response to determining that the respective reputation score exceeds the threshold, and may refrain from adding the mapping in response to determining that the respective reputation score does not exceed the threshold.

There are other scenarios where the processor may adjust a ranking based on parameters that are additional to the specificity scores of each molecule. In some embodiments, the processor may adjust a ranking based on whether the processor determines a given molecule to be associated with an adverse drug reaction, or whether the processor determines the given molecule is associated with an adverse drug reaction when applied to the pre-specified biological features. In some embodiments, in response to a mention being detected during the searching, the processor accesses a database of known adverse drug reactions, and determines, based on entries of the database, whether the given molecule is associated with an adverse drug reaction. In other embodiments, the processor determines whether the mention itself indicates an adverse drug reaction in connection with the given molecule (e.g., by detecting a negative connotation in the mention).

In response to detecting the adverse drug reaction, the processor may generate a flag in the mapping (e.g., in an additional column of table 200 that indicates whether the molecule is associated with an adverse drug reaction). The processor may, when generating the ranking or after generating the ranking, adjust the ranking to reduce the rank of molecules associated with adverse drug reactions. The reduction may be determined based on severity of the adverse drug reaction (e.g., as determined by referencing the database), or may be a flat reduction whenever an adverse drug reaction is detected. In some embodiments, the processor may exclude a molecule from the ranking if the molecule is associated with an adverse drug reaction (e.g., based on the request indicating such an exclusion).

As an additional factor that the processor may use to influence rankings, in some embodiments, the processor determines a number of publications in which a molecule, a biological feature, and a concrete instance are mentioned in connection with one another, and increases the ranking of the molecule relative to other molecules of the plurality of molecules based on the number of publications. The processor may perform this positive weighting because the processor may determine that the molecule mappings indicate that a particular molecule is more frequently cited in more reliable (prestigious) publications.

In some embodiments, pre-processing may be implemented in order to improve the speed at which the processor performs the searching. For example, some biological features may be so commonly searched or so prevalent, that the processor considers those biological features to be common. The processor may pre-search known publications based on common biological features, and may generate a graph that maps pre-searched biological features to molecules and concrete instances as found during the pre-search. Thus, when the processor performs a search, the processor may determine whether the pre-specified plurality of biological features comprise a common biological feature, and, if so, the processor may search the graph instead of the publications themselves. The processor may additionally determine whether new publications have become known since the time that the pre-search was performed, and in response to determining that new publications are available, the processor may search those new publications. This results in the processor more efficiently performing the search, as every publication need not be searched when the request includes pre-specified biological features that are common.

Further, when the processor is searching an uncommon biological feature (or a common biological feature in new publications), and the processor determines that search results exist with a qualifying mention, the processor may add the mapping derived from that mention to the graph. Thus, the processor may iteratively improve the graph as new searches are performed, which incrementally improves the degree to which the pre-search can be relied upon as the processor receives future requests.

Network Architecture

Figure 3:
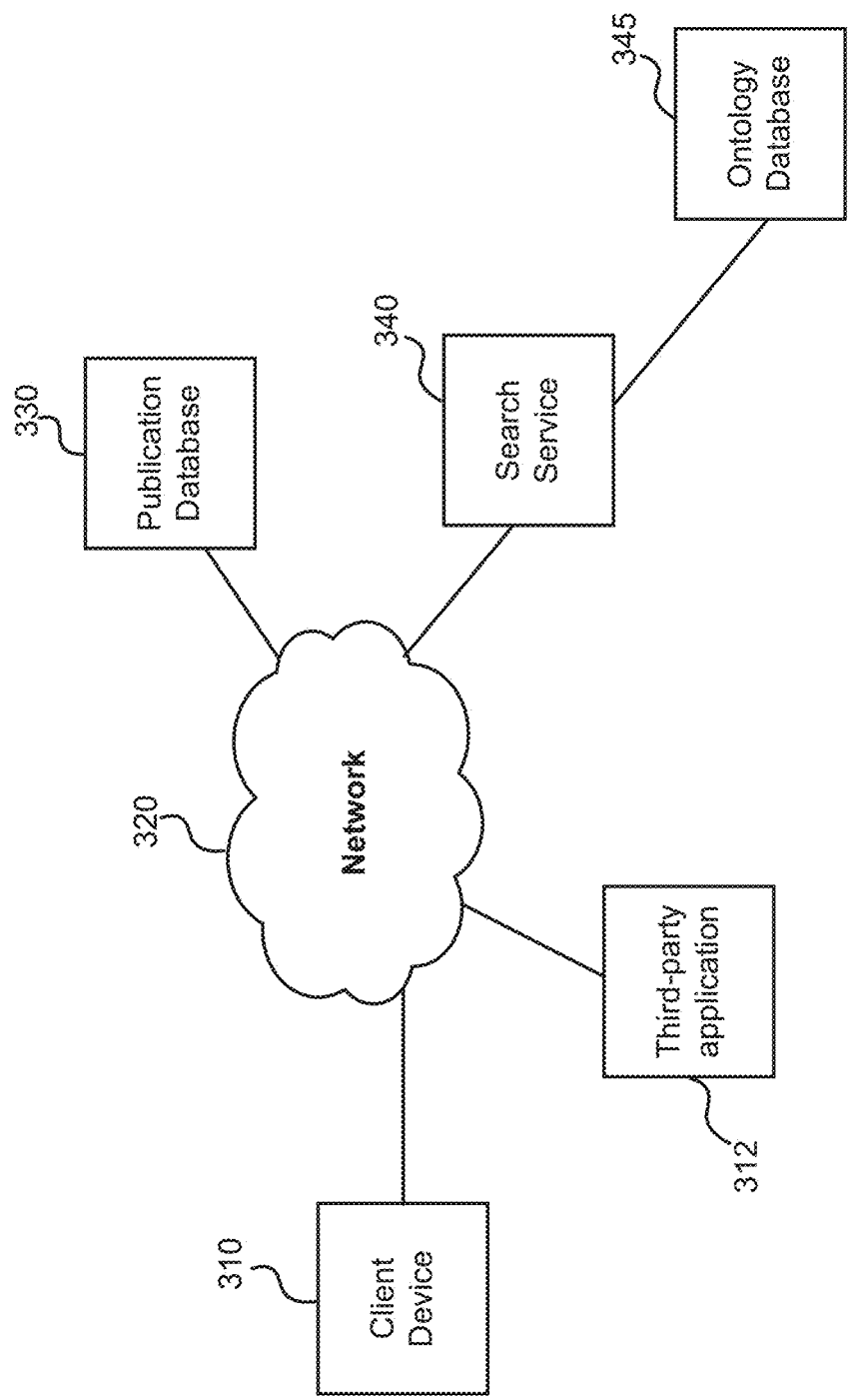
FIG. 3 illustrates one embodiment of a network diagram including various components used in procuring a specificity-based ranking of molecules, in accordance with some embodiments of the disclosure.

FIG. 3 illustrates one embodiment of a network diagram including various components used in procuring a specificity-based ranking of molecules, in accordance with some embodiments of the disclosure. FIG. 3 depicts client device 310 and third-party application 312, each of which may generate a request to search for molecules that correspond to a pre-specified plurality of biological features, in accordance with the foregoing disclosure on how the request is created. The request is transmitted over network 320, which may be any network, such as those networks described below with respect to FIG. 5. Search service 340 houses the processor described herein, which performs the operations relating to receiving and processing the request. The processor itself is described in further detail with respect to FIG. 5 below. Ontology database 345 includes a storage of the above-described ontology. While depicted as being part of the search service 340, ontology database 345 may be a third-party database, and may be accessed by search service 340 by way of a query transmitted over network 320. While only one ontology database 345 is depicted, this is merely for convenience; two or more ontology databases may be referenced by search service 340. FIG. 5 also depicts publication database 330, which search service 340 may query (e.g., by way of network 320) when searching publications in accordance with the foregoing. While only one publication database 330 is depicted, this is merely for convenience; two or more publication databases may be referenced by search service 340.

Search Service Architecture

Figure 4:
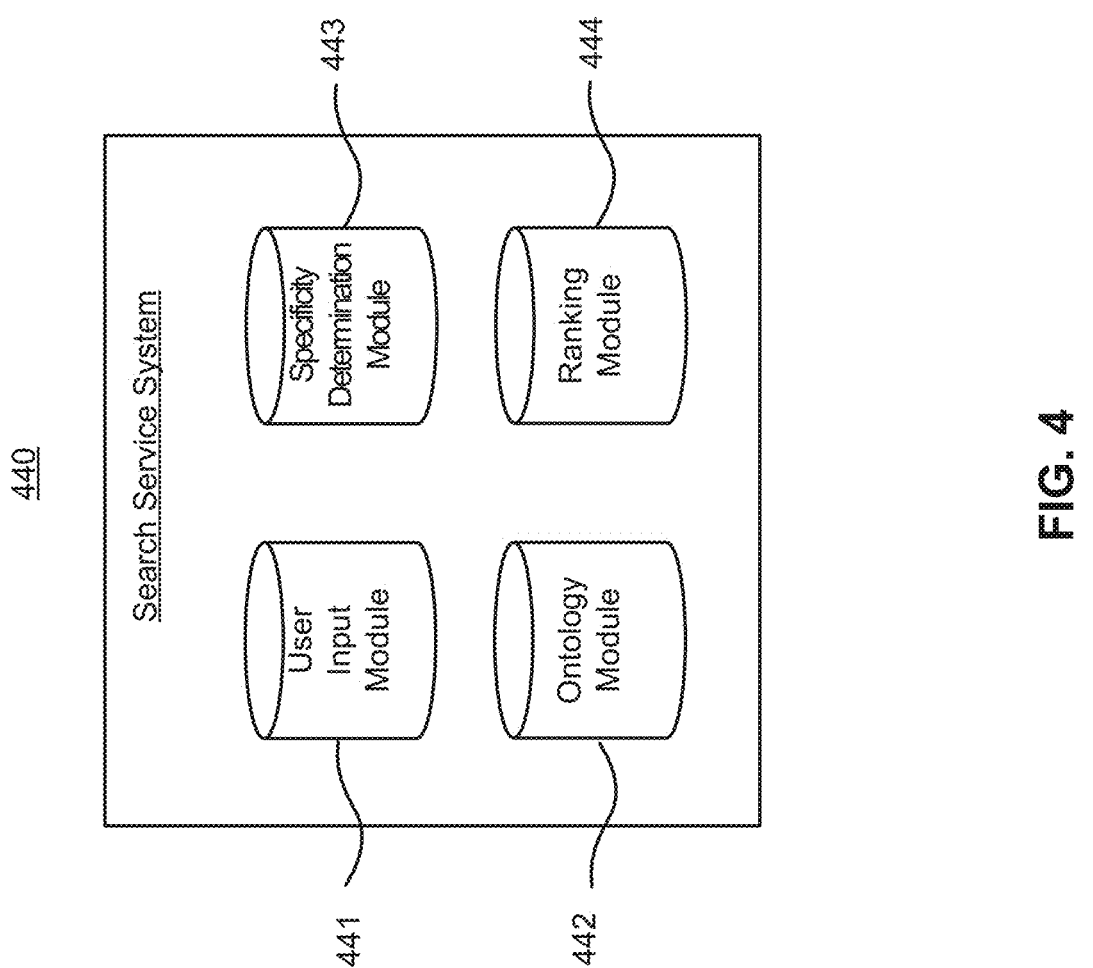
FIG. 4 illustrates one embodiment of an architecture of a search service used to procure a specificity-based ranking of molecules, in accordance with some embodiments of the disclosure.

FIG. 4 illustrates one embodiment of an architecture of a search service system 400 used to procure a specificity-based ranking of molecules, in accordance with some embodiments of the disclosure. Search service system 440 (which corresponds to search service 340 of FIG. 3) includes user input module 441, an ontology module 442, a specificity determination module 443 and a ranking module 444. User input module 441 processes user input (e.g., keyword input, option selection, molecule selection, etc. as described above) received in connection with a search query. Ontology module 442 maps the user input to additional parameters to search, such as additional biological features, concrete instances, and the like, as described in the foregoing. Specificity determination module 443 determines the specificity of each molecule, as described in the foregoing. Ranking module 444 ranks the molecules based on the specificity of the molecules, as described in the foregoing.

User input module 441 may be executed by the processor of search service 440 to generate for display a form for collecting user input (e.g., at client device 310), and to parse input received from the user by way of a search request received by the processor. When performing a requested search, the processor may execute ontology module 442 to supplement biological features specified by the user input (or by a third-party application where the biological features are not based on user input). The processor executes specificity determination module 443 to determine a specificity score for each molecule mapped as a result of the searching. The processor executes ranking module 444, which ranks the molecules at least based on specificity, and perhaps based on additional parameters and weights as discussed in the foregoing. The processor outputs the ranking computed by the ranking module 444 (e.g., for display at client device 310).

Computing Machine Architecture

FIG. 5 is a block diagram illustrating components of an example machine able to read instructions from a machine-readable medium and execute them in a processor (or controller). Specifically, FIG. 5 shows a diagrammatic representation of a machine in the example form of a computer system 500 within which program code (e.g., software) for causing the machine to perform any one or more of the methodologies and systems discussed with FIGS. 1-4 herein may be executed. The program code may be comprised of instructions 524 executable by one or more processors 502. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 524 (sequential or otherwise) that specify actions to be taken by that machine. Further, while only a single machine is illustrated, the term "machine" shall also be taken to include any collection of machines that individually or jointly execute instructions 524 to perform any one or more of the methodologies discussed herein.

The example computer system 500 includes a processor 502 (e.g., a central processing unit (CPU), a graphics processing unit (GPU), a digital signal processor (DSP), one or more application specific integrated circuits (ASICs), one or more radio-frequency integrated circuits (RFICs), or any combination of these; also referred to interchangeably as "processing circuitry"), a main memory 504, and a static memory 506, which are configured to communicate with each other via a bus 508. The computer system 500 may further include visual display interface 510. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 510 may include or may interface with a touch enabled screen. The computer system 500 may also include alphanumeric input device 512 (e.g., a keyboard or touch screen keyboard), a cursor control device 514 (e.g., a mouse, a trackball, a joystick, a motion sensor, or other pointing instrument), a storage unit 516, a signal generation device 518 (e.g., a speaker), and a network interface device 520, which also are configured to communicate via the bus 508.

The storage unit 516 includes a machine-readable medium 522 on which is stored instructions 524 (e.g., software) embodying any one or more of the methodologies or functions described herein. The instructions 524 (e.g., software) may also reside, completely or at least partially, within the main memory 504 or within the processor 502 (e.g., within a processor's cache memory) during execution thereof by the computer system 500, the main memory 504 and the processor 502 also constituting machine-readable media. The instructions 524 (e.g., software) may be transmitted or received over a network 526 via the network interface device 520.

While machine-readable medium 522 is shown in an example embodiment to be a single medium, the term "machine-readable medium" should be taken to include a single medium or multiple media (e.g., a centralized or distributed database, or associated caches and servers) able to store instructions (e.g., instructions 524). The term "machine-readable medium" shall also be taken to include any medium that is capable of storing instructions (e.g., instructions 524) for execution by the machine and that cause the machine to perform any one or more of the methodologies disclosed herein. The term "machine-readable medium" includes, but not be limited to, data repositories in the form of solid-state memories, optical media, and magnetic media.

Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for generating a specificity-based ranking of therapeutic molecules through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for searching and ranking molecules based on specificity, the method comprising:
  receiving a request to search for molecules that correspond to a pre-specified plurality of biological features;
  generating a data structure that maps a plurality of molecules to the plurality of pre-specified biological features by:
    searching publications for a reference to a concrete instance corresponding to a biological feature of the pre-specified plurality of biological features in connection with a molecule, and
    in response to detecting, during the searching, a given reference to a given concrete instance corresponding to a given biological feature in connection with a given molecule, adding a mapping between the given molecule, the given biological feature, and the given concrete instance to the data structure;

determining a respective specificity score for each respective molecule of the plurality of molecules by:

determining which of the plurality of biological features are mapped to the respective molecule; and for each respective biological feature of the plurality of biological features that are mapped to the respective molecule:

determining whether more than one concrete instance corresponding to the respective specified biological feature is mapped to the respective molecule; and in response to determining that there is not more than one concrete instance corresponding to the respective biological feature that is mapped to the respective molecule, incrementing the respective specificity score by a unit;

generating a ranking of the plurality of molecules based on each respective specificity score for each respective molecule of the plurality of molecules; and outputting the ranking.

2. The method of claim 1, wherein searching publications for a reference to a concrete instance corresponding to a biological feature of the pre-specified plurality of biological features in connection with a molecule comprises:

transmitting the pre-specified plurality of biological features into an ontology;

receiving an output of additional biological features from the ontology; and searching publications for a reference to either a concrete instance corresponding to a biological feature of the pre-specified plurality of biological features in connection with a molecule, or a reference to a concrete instance corresponding to an additional biological feature of the additional biological features in connection with a molecule.

3. The method of claim 2, wherein searching publications for a reference to a concrete instance corresponding to a biological feature of the pre-specified plurality of biological features in connection with a molecule further comprises:

applying a machine learning algorithm to detect an obscured reference to a concrete instance corresponding to a biological feature of the pre-specified plurality of biological features in connection with a molecule, notwithstanding that the obscured reference neither matches a pre-specified biological feature of the plurality of biological features nor an additional biological feature of the additional biological features.

4. The method of claim 1, wherein determining the respective specificity score for each respective molecule of the plurality of molecules further comprises:

in response to determining that there is more than one concrete instance corresponding to the respective biological feature that is mapped to the respective molecule, determining a number of concrete instances corresponding to the respective biological feature that is mapped to the respective molecule; and incrementing the respective specificity score by an amount smaller than the unit, wherein the amount is inversely proportional to the number.

5. The method of claim 1, wherein generating the ranking of the plurality of molecules further comprises:

determining a reputation score for each publication in which each respective molecule of the plurality of molecules was referenced;

generating weighted specificity scores by applying a weight to each respective specificity score of each respective molecule based on an aggregation of each reputation score corresponding to a publication in which the respective molecule was referenced; and generating the ranking based on the weighted specificity scores.

6. The method of claim 5, further comprising, further in response to detecting, during the searching, a reference to a given concrete instance corresponding to a given biological feature in connection with a given molecule:

determining whether a respective reputation score from a publication comprising the reference exceeds a threshold, wherein adding the mapping between the given molecule, the given biological feature, and the given concrete instance to the data structure is performed in response to determining that the respective reputation score exceeds the threshold; and in response to determining that the respective reputation score does not exceed the threshold, refraining from adding the mapping between the given molecule, the given biological feature, and the given concrete instance to the data structure.

7. The method of claim 1, wherein the method further comprises, further in response to detecting, during the searching, a given reference to a given concrete instance corresponding to a given biological feature in connection with a given molecule:

determining whether the given reference indicates an adverse drug reaction in connection with the given molecule;

in response to determining that the given reference indicates an adverse drug reaction in connection with the given molecule, including a flag in the mapping corresponding to the given molecule; and wherein outputting the ranking to the user comprises:

adjusting the ranking to reduce the rank of the given molecule based on the flag; and outputting the adjusted ranking.

8. The method of claim 1, wherein generating the ranking further comprises:

determining a number of publications in which a molecule of the plurality of molecules, a biological feature, and a concrete instance are referenced in connection with one another; and increasing the ranking of the molecule relative to other molecules of the plurality of molecules based on the number of publications.

9. The method of claim 1, wherein the publications were pre-searched based on common biological features, and wherein a graph was created that maps pre-searched biological features to molecules and concrete instances, and wherein searching the publications for the reference to a concrete instance corresponding to a biological feature of the pre-specified plurality of biological features in connection with a molecule comprises:

determining whether the pre-specified plurality of biological features comprise a common biological feature; and in response to determining that the pre-specified plurality of biological features comprise the common biological feature, searching the graph instead of the publications themselves.

10. The method of claim 9, further comprising:

in response to determining that the pre-specified plurality of biological features does not comprise the common biological feature:

searching the publications themselves; and in response to detecting, during the searching, a given reference to a given concrete instance corresponding to a given biological feature in connection with a given molecule, adding the mapping to the graph.

11. A system for searching and ranking molecules based on specificity, the system comprising:

communications circuitry; and processing circuitry configured to:

receive, using the communications circuitry, a request to search for molecules that correspond to a pre-specified plurality of biological features;

generate a data structure that maps a plurality of molecules to the plurality of pre-specified biological features by:

searching publications for a reference to a concrete instance corresponding to a biological feature of the pre-specified plurality of biological features in connection with a molecule, and in response to detecting, during the searching, a given reference to a given concrete instance corresponding to a given biological feature in connection with a given molecule, adding a mapping between the given molecule, the given biological feature, and the given concrete instance to the data structure;

determine a respective specificity score for each respective molecule of the plurality of molecules by, for each respective molecule of the plurality of molecules:

determining which of the plurality of biological features are mapped to the respective molecule; and for each respective biological feature of the plurality of biological features that are mapped to the respective molecule:

determining whether more than one concrete instance corresponding to the respective specified biological feature is mapped to the respective molecule; and in response to determining that there is not more than one concrete instance corresponding to the respective biological feature that is mapped to the respective molecule, incrementing the respective specificity score by a unit;

generate a ranking of the plurality of molecules based on each respective specificity score for each respective molecule of the plurality of molecules; and output the ranking.

12. The system of claim 11, wherein the processing circuitry is, when searching publications for a reference to a concrete instance corresponding to a biological feature of the pre-specified plurality of biological features in connection with a molecule, further configured to:

transmit the pre-specified plurality of biological features into an ontology;

receive an output of additional biological features from the ontology; and search publications for a reference to either a concrete instance corresponding to a biological feature of the pre-specified plurality of biological features in connection with a molecule, or a reference to a concrete instance corresponding to an additional biological feature of the additional biological features in connection with a molecule.

13. The system of claim 12, wherein the processing circuitry is, when searching publications for a reference to a concrete instance corresponding to a biological feature of the pre-specified plurality of biological features in connection with a molecule, further configured to:

apply a machine learning algorithm to detect an obscured reference to a concrete instance corresponding to a biological feature of the pre-specified plurality of biological features in connection with a molecule, notwithstanding that the obscured reference neither matches a pre-specified biological feature of the plurality of biological features nor an additional biological feature of the additional biological features.

14. The system of claim 11, wherein the processing circuitry is, when determining the respective specificity score for each respective molecule of the plurality of molecules, further configured to:

in response to determining that there is more than one concrete instance corresponding to the respective biological feature that is mapped to the respective molecule, determine a number of concrete instances corresponding to the respective biological feature that is mapped to the respective molecule; and increment the respective specificity score by an amount smaller than the unit, wherein the amount is inversely proportional to the number.

15. The system of claim 11, wherein the processing circuitry is, when generating the ranking of the plurality of molecules, further configured to:

determine a reputation score for each publication in which each respective molecule of the plurality of molecules was referenced;

generate weighted specificity scores by applying a weight to each respective specificity score of each respective molecule based on an aggregation of each reputation score corresponding to a publication in which the respective molecule was referenced; and generate the ranking based on the weighted specificity scores.

16. The system of claim 15, wherein the processing circuitry is, further in response to detecting, during the searching, a reference to a given concrete instance corresponding to a given biological feature in connection with a given molecule, further configured to:

determine whether a respective reputation score from a publication comprising the reference exceeds a threshold, wherein adding the mapping between the given molecule, the given biological feature, and the given concrete instance to the data structure is performed in response to determining that the respective reputation score exceeds the threshold; and in response to determining that the respective reputation score does not exceed the threshold, refrain from adding the mapping between the given molecule, the given biological feature, and the given concrete instance to the data structure.

17. The system of claim 11, wherein the processing circuitry is, further in response to detecting, during the searching, a given reference to a given concrete instance corresponding to a given biological feature in connection with a given molecule, further configured to:

determine whether the given reference indicates an adverse drug reaction in connection with the given molecule;

in response to determining that the given reference indicates an adverse drug reaction in connection with the given molecule, include a flag in the mapping corresponding to the given molecule; and wherein the processing circuitry is further configured, when outputting the ranking to the user, to:

adjust the ranking to reduce the rank of the given molecule based on the flag; and
output the adjusted ranking.

18. The system of claim 11, wherein the processing circuitry is, when generating the ranking, further configured to:
   determine a number of publications in which a molecule of the plurality of molecules, a biological feature, and a concrete instance are referenced in connection with one another; and
   increase the ranking of the molecule relative to other molecules of the plurality of molecules based on the number of publications.

19. The system of claim 11, wherein the publications were pre-searched based on common biological features, wherein a graph was created that maps pre-searched biological features to molecules and concrete instances, wherein the processing circuitry is, when searching the publications for the reference to a concrete instance corresponding to a biological feature of the pre-specified plurality of biological features in connection with a molecule, further configured to:
   determine whether the pre-specified plurality of biological features comprise a common biological feature; and
   in response to determining that the pre-specified plurality of biological features comprise the common biological feature, search the graph instead of the publications themselves, and wherein
   the processing circuitry is further configured to, in response to determining that the pre-specified plurality of biological features does not comprise the common biological feature:
      search the publications themselves; and
      in response to detecting, during the searching, a given reference to a given concrete instance corresponding to a given biological feature in connection with a given molecule, add the mapping to the graph.

20. A non-transitory computer-readable medium configured to store instructions, the instructions when executed by a processor cause the processor to:
   receive, using the communications circuitry, a request to search for molecules that correspond to a pre-specified plurality of biological features;
   generate a data structure that maps a plurality of molecules to the plurality of pre-specified biological features by:
      searching publications for a reference to a concrete instance corresponding to a biological feature of the pre-specified plurality of biological features in connection with a molecule, and
      in response to detecting, during the searching, a given reference to a given concrete instance corresponding to a given biological feature in connection with a given molecule, adding a mapping between the given molecule, the given biological feature, and the given concrete instance to the data structure;
   determine a respective specificity score for each respective molecule of the plurality of molecules by, for each respective molecule of the plurality of molecules:
      determining which of the plurality of biological features are mapped to the respective molecule; and
      for each respective biological feature of the plurality of biological features that are mapped to the respective molecule:
         determining whether more than one concrete instance corresponding to the respective specified biological feature is mapped to the respective molecule; and
         in response to determining that there is not more than one concrete instance corresponding to the respective biological feature that is mapped to the respective molecule, incrementing the respective specificity score by a unit;
   generate a ranking of the plurality of molecules based on each respective specificity score for each respective molecule of the plurality of molecules; and
   output the ranking.

* * * * *